US008859764B2

(12) United States Patent
Mash et al.

(10) Patent No.: US 8,859,764 B2
(45) Date of Patent: Oct. 14, 2014

(54) METHODS AND COMPOSITIONS FOR PREPARING NORIBOGAINE FROM VOACANGINE

(75) Inventors: Deborah C. Mash, Miami, CA (US); Robert M. Moriarty, Michiana Shores, IN (US); Richard D. Gless, Jr., Oakland, CA (US)

(73) Assignee: DemeRx, Inc., Ft. Lauderdale, FL (US)

( * ) Notice: Subject to any disclaimer, the term of this patent is extended or adjusted under 35 U.S.C. 154(b) by 0 days.

(21) Appl. No.: 13/496,185

(22) PCT Filed: Jan. 23, 2012

(86) PCT No.: PCT/US2012/022255
§ 371 (c)(1),
(2), (4) Date: Sep. 5, 2012

(87) PCT Pub. No.: WO2012/103028
PCT Pub. Date: Aug. 2, 2012

(65) Prior Publication Data
US 2013/0303756 A1    Nov. 14, 2013

Related U.S. Application Data

(60) Provisional application No. 61/436,511, filed on Jan. 26, 2011, provisional application No. 61/453,884, filed on Mar. 17, 2011, provisional application No. 61/454,904, filed on Mar. 21, 2011.

(51) Int. Cl.
*C07D 453/06* (2006.01)
*C07D 487/18* (2006.01)
*C07D 471/22* (2006.01)

(52) U.S. Cl.
CPC ............ *C07D 471/22* (2013.01); *C07D 487/18* (2013.01)
USPC ........................................................ 540/579

(58) Field of Classification Search
CPC .................................................... C07D 453/06
USPC ........................................................ 540/579
See application file for complete search history.

(56) References Cited

U.S. PATENT DOCUMENTS

| | | |
|---|---|---|
| 2,813,873 A | 11/1957 | Janot et al. |
| 3,516,989 A | 6/1970 | Sallay |
| 3,557,126 A | 1/1971 | Sallay |
| 3,574,220 A | 4/1971 | Sallay |
| 3,639,408 A | 2/1972 | Nagata et al. |
| 3,715,361 A | 2/1973 | Epstein et al. |
| 3,875,011 A | 4/1975 | Rubenstein et al. |
| 4,107,288 A | 8/1978 | Oppenheim et al. |
| 4,272,541 A | 6/1981 | Kotick et al. |
| 4,375,414 A | 3/1983 | Strahilevitz |
| 4,444,758 A | 4/1984 | Scherschlicht et al. |
| 4,462,941 A | 7/1984 | Lee et al. |
| 4,464,378 A | 8/1984 | Hussain |
| 4,499,096 A | 2/1985 | Lotsof |
| 4,573,995 A | 3/1986 | Chen et al. |
| 4,587,243 A | 5/1986 | Lotsof |
| 4,604,365 A | 8/1986 | O'Neill et al. |
| 4,620,977 A | 11/1986 | Strahilevitz |
| 4,626,539 A | 12/1986 | Aungst et al. |
| 4,661,492 A | 4/1987 | Lewis et al. |
| 4,668,232 A | 5/1987 | Cordes et al. |
| 4,737,586 A | 4/1988 | Potier et al. |
| 4,806,341 A | 2/1989 | Chien et al. |
| 4,857,523 A | 8/1989 | Lotsof |
| 5,026,697 A | 6/1991 | Lotsof |
| 5,075,341 A | 12/1991 | Mendelson et al. |
| 5,145,684 A | 9/1992 | Liversidge et al. |
| 5,149,538 A | 9/1992 | Granger et al. |
| 5,152,994 A | 10/1992 | Lotsof |
| 5,283,247 A | 2/1994 | Dwivedi et al. |
| 5,290,784 A | 3/1994 | Qu et al. |
| 5,316,759 A | 5/1994 | Rose et al. |
| 5,382,657 A | 1/1995 | Karasiewicz et al. |
| 5,426,112 A | 6/1995 | Zagon et al. |
| 5,552,406 A | 9/1996 | Mendelson et al. |
| 5,574,052 A | 11/1996 | Rose et al. |
| 5,578,645 A | 11/1996 | Askanazi et al. |
| 5,580,876 A | 12/1996 | Crain et al. |
| 5,591,738 A | 1/1997 | Lotsof |
| 5,618,555 A | 4/1997 | Tokuda et al. |
| 5,703,101 A | 12/1997 | Rose et al. |
| 5,726,190 A | 3/1998 | Rose et al. |
| 5,760,044 A | 6/1998 | Archer |
| 5,861,422 A | 1/1999 | Rose et al. |
| 5,865,444 A | 2/1999 | Kempf et al. |
| 5,925,634 A | 7/1999 | Olney |
| 5,935,975 A | 8/1999 | Rose et al. |
| 6,211,360 B1 | 4/2001 | Glick et al. |
| 6,291,675 B1 | 9/2001 | Coop et al. |

(Continued)

FOREIGN PATENT DOCUMENTS

| | | |
|---|---|---|
| CA | 2039197 | 9/1995 |
| DE | 22 17 132 | 10/1972 |

(Continued)

OTHER PUBLICATIONS

U.S. Appl. No. 13/104,406, filed May 10, 2011, Mash et al.
U.S. Appl. No. 13/165,626, filed Jun. 21, 2011, Mash, Deborah C.
U.S. Appl. No. 13/165,639, filed Jun. 21, 2011, Mash et al.
U.S. Appl. No. 13/165,642, filed Jun. 21, 2011, Mash et al.
U.S. Appl. No. 13/198,593, filed Nov. 7, 2011, Mash et al.
U.S. Appl. No. 13/383,405, Moriarty, Robert.
U.S. Appl. No. 13/496,185, Mash, Deborah C.
Ala-Hurula et al. "Erogotamine Abuse: Results of Ergotamine Discontinuation, with Special Reference to the Plasma Concentrations", Cephalalgia, 2/4: abstract only, 1982.
Ala-Hurula et al. "Tolfenamic Acid and Ergotamine Abuse", Headache: The Journal of Head and Face Pain, 21(6): abstract only, 1981.
Alexander. "A Procedure for Drug Screening Without the Need to Transport Urines Use of Ion Exchange Papers and Hem Agglutination Inhibition", Clin Toxicol, 9(3): abstract only, 1976.

(Continued)

*Primary Examiner* — Brenda Coleman
(74) *Attorney, Agent, or Firm* — Foley & Lardner LLP

(57) ABSTRACT

Disclosed are methods and compositions for preparing and purifying the non-addictive alkaloid noribogaine.

4 Claims, No Drawings

(56) References Cited

U.S. PATENT DOCUMENTS

| | | | |
|---|---|---|---|
| 6,348,456 | B1 | 2/2002 | Mash et al. |
| 6,451,806 | B2 | 9/2002 | Farrar |
| 6,806,291 | B1 | 10/2004 | Sunkel et al. |
| 6,864,271 | B2 | 3/2005 | Bazan et al. |
| 7,220,737 | B1 | 5/2007 | Mash |
| 7,737,169 | B2 | 6/2010 | Corrie et al. |
| 7,745,479 | B2 | 6/2010 | Nettekoven et al. |
| 7,754,710 | B2 | 7/2010 | Mash |
| 8,178,524 | B2 | 5/2012 | Mash |
| 8,362,007 | B1 | 1/2013 | Mash et al. |
| 2003/0153552 | A1 | 8/2003 | Mash et al. |
| 2003/0158202 | A1 | 8/2003 | Caldirola et al. |
| 2006/0051317 | A1 | 3/2006 | Batrakova et al. |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2013/0072472 | A1 | 3/2013 | Gless et al. |

FOREIGN PATENT DOCUMENTS

| | | |
|---|---|---|
| GB | 0 841 697 | 7/1960 |
| GB | 0 924 042 | 4/1963 |
| GB | 1 256 914 | 12/1971 |
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |

OTHER PUBLICATIONS

Alim et al. "Open-Label, Dose Run-Up Study of Diethylpropion in Initial Cocaine Abstinence", Clinical Neuropharmacology, 17(2): abstract only, 1994.

Almeida. "Use and Abuse of Alcohol and Drugs a Clinical Study of Certain Aspects of Their Interrelationship", Bol of Sanit Panam, 88(1), abstract only, 1980.

Al-Shabanah et al. "Gastric Antiulcer and Cytoprotective Effects of Cathinone, a Psychoactive Alkaloid of Khat (Catha Edulis Forsk.) and Amphetamine in Rats", Regulatory Peptides, abstract only, 1994.

Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.

Bagal et al. "Modulation of Morphine-Induced Antinociception by Ibogaine and Noribogaine", Brain Research, 741(1-2): pp. 258-262, 1996.

Ban. "Adverse Effects to Psychotomimetics. Proposition of a Psychopharmacological Classification", In: Radouco-Thomas S, ed. Pharmacologie, Toxicologie, et abus des psychotomimetiques (hallucinogens)., QV 109: abstract only, 1974.

Bartlett et al. "The Alkaloids of Tabernanthe iboga. Part IV..sup.1 The Structures of Ibogamine, Ibogaine, Tabernanthine and Voacangine", J. Am. Chem. Soc., 80: pp. 126-136, 1958.

Batrakova. "Pluronic P85 Enhances the Delivery of Digoxin to the Brain: In Vitro and In Vivo Studies", The J. of Pharm. and Exp. Thera, 296, p. 551-557, 2001.

Baumann et al. "Comparative Neurobiology of Ibogaine and its Metabolite, 12-Hydroxyibogaimine (Noribogaine), in Rodents." Conference at New York University, Abstract only, 2001.

Beaubrun. "The Diagnosis and Management of Acute Psychotic Reaction Due to Alcohol and Drugs", Caribb Med J, 36(1): abstract only, 1975.

Beck et al. "Energy-Dependent Reduced Drug Binding as a Mechanism of Vinca Alkaloid Resistance in Human Leukemic Lymphoblasts", Mol Pharmacol, 24(3): abstract only, 1983.

Benet et al. "Pharmacokinetics: Biotransformation of Drugs." in Gilman et al. Goodman and Gilman's the Pharmacological Basis of Therapeutics (1990) :13-16.

Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.

Bert et al. "Non-Amphetaminic Central Stimulation by Alkaloids from the Ibogaine and Vobasine Series", Planta Med., 54(3): abstract only, 1988.

Bhargava et al. "Effects of ibogaine and noribogaine on the antinociceptive action of mu-, delta- and kappa-opioid receptor agonists in mice", Brain Research 752:234-238, 1997.

Blum et al. "Peyote a Potential Ethnopharmacologic Agent for Alcoholism and Other Drug Dependencies Possible Biochemical Rationale", Clin Toxicol, 11(4): abstract only, 1977.

Blum et al. "Possible Role of Tetrahydroisoquinoline Alkaloids in Postalcohol Intoxication States", Ann N Y Acad Sci, 273: abstract only, 1976.

Blum et al. "Putative Role of Isoquinoline Alkaloids in Alcoholism: A Link to Opiates", Alcohol Clin Exp Res, 2(2): abstract only, 1978.

Brady et al. "Analgesic Effects of Intraventricular Morphine and Enkephalins in Nondependent and Morphine-Dependent Rats", J. Pharmacol. Exp. Ther., 222(1): abstract only, 1982.

Buchi et al. "The total synthesis of iboga alkaloids", J. Am. Chem. Soc. vol. 88, p. 3099-3109, 1966.

Bundgaard. "Design of Prodrugs: Bioreversible Derivatives for Various Functional Groups and Chemical Entities." Design of Prodrugs, 1-10, 1985.

Bussel et al. "Isolated Thrombocytopenia in Patients Infected with HIV Treatment with Intravenous Gamma Globulin", Am J Hematol, 28(2): abstract only, 1988.

Caldwell et al. "The Biochemical Pharmacology of Abused Drugs. III. Cannabis, Opiates, and Synthetic Narcotics", Clin. Pharmacol. Ther., 16/6: abstract only, 1974.

Cankat. "Pharmacological Aspects of Drug Induced Headache", Funct. Neurol., 7/6: abstract only, 1992.

Cappendijk et al. "Inhibitory Effects of Ibogaine on Cocaine Self-Administration in Rats", Eur. J. Pharmacol., 241 (2-3): abstract only, 1993.

Cappendijk et al. "The Inhibitory Effect of Norharman on Morphine Withdrawal Syndrome in Rats: Comparisons with Ibogaine", Behavioural Brain Research, pp. 1-3, 1994.

Castle. "Drugs and Fibrotic Reactions—Part I", Adverse Drug React. Bull., 113: abstract only, 1985.

Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry, 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.

Cherny et al. "Opioid responsiveness of cancer pain syndromes caused by neuropathic or nociceptive mechanisms: a combined analysis of controlled, single-dose studies", Neurobiology 44:857-861, 1994.

Cheze et al. "Determination of ibogaine and noribogaine in biological fluids and hair by LC-MS/MS after Tabernanthe iboga abuse", Forensic Science International, Elsevier Scientific Publishers Ireland Ltd, IE, vol. 176. No. 1, pp. 58-66, 2007.

Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.

Damstrup et al. "Retroperitoneal Fibrosis After Long-Term Daily Use of Ergotamine", Int. Urol. Nephrol., 18/3: abstract only, 1986.

Deecher et al. "Mechanisms of Action of Ibogaine and Harmaline Congeners Based on Radioligand Binding Studies", Brain Research, 571(2): pp. 242-247, 1992.

Diener et al. "Analgesic-Induced Chronic Headache Long-Term Results of Withdrawal Therapy", J Neurol, 236(1): abstract only, 1989.

(56) References Cited

OTHER PUBLICATIONS

Dierckx et al. "Intraarterial Sodium Nitroprusside Infusion in the Treatment of Severe Ergotism", Clin. Neuropharmacol., 9/6: abstract only, 1986.

Dzoljic et al. "Effect of Ibogaine on Naloxone-Precipitated Withdrawal Syndrome in Chronic Morphine-Dependent Rats", Arch. Int. Pharmacodyn., 294:64-70, 1988.

Eberwine et al. "Molecular Analysis of Cellular Responses to Opiate Use", Fidia Res. Found. Symp. Ser., 7(Neurotransm. Regul. Gene Transcr.): abstract only, 1991.

Elkind. "Drug Abuse and Headache", Med Clin North Am, 75(3): abstract only, 1991.

Evenson. "Developments in Therapeutic Drug Monitoring and Alkaloid Analysis", Fed Proc, 34(12): abstract only, 1975.

Faglia et al. "Dihydroergocryptine in Management of Microprolactinomas", J Clin Endocrinol Metab, 65(4): abstract only, 1987.

Fairchild et al. "Keynote Address: Multidrug Resistance: A Pleiotropic Response to Cytotoxic Drugs", Int. J. Radiat. Oncol. Biol. Phys., 20/2: abstract only, 1991.

Finkle. "Phencyclidine Identification by Thin-Layer Chromatography. A Rapid Screening Procedure for Emergency Toxicology", Am. J. Clin. Pathol., 70/2: abstract only, 1978.

Fonne Pfister of al. "Xenobiotic and Endobiotic Inhibitors of Cytochrome P-450dbl Function, the Target of the Debrisoquine / Sparteine Type Polymorphism", Biochem. Pharmacol., 37(20): abstract only, 1988.

Frances et al. "Effects of Ibogaine on Naloxone-Precipitated Withdrawal in Morphine-Dependent Mice", Fundam Clin Pharmacol, 6(8-9): abstract only, 1992.

Gabr et al. "Changes in Absolute Amount of Alkaloids in Datura-Metel Treated with Certain Growth Regulators", Herba Pol, 21(2): abstract only, 1975.

Garcia et al. "Chronic pain states: pathophysiology and medical therapy", Seminars in Arthritis and Rheumatism, 27:1-16, 1997.

Gennaro. "Remington: The Science and Practice of Pharmacy", Mack Publishing Col., vol. II, pp. 1736 & 1814, 1995.

George et al. "Palliative medicine", Postgrad, Med. Journal, vol. 69, pp. 426-449, 1993.

Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.

Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.

Glick et al. "Effect of Ibogaine on Acute Signs of Morphine Withdrawal in Rats: Independence from Tremor", Neuropharmacology, 31/5: abstract only, 1992.

Glick et al. "Effects of Aftereffects of Ibogaine on Morphine Self-Administration in Rats", European Journal of Pharmacology, 195(3): abstract only, 1991.

Glick et al. "Ibogaine-like effects of noribogaine in rats", Brain Research, 713:294-297, 1996.

Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.

Gold et al. "Effect of Methadone Dosage on Clonidine Detoxification Efficacy", Am. J. Psychiatry, 137/3: abstract only, 1980.

Gothoni. "Harmine-, Lon-954- and 5-Hydroxytryptophan-Induced Tremors in Rats Withdrawn from Ethanol", Acta Pharmacol Toxicol, 57(1): abstract only, 1985.

Gross. "Effect of Ergot Alkaloids on Serum Prolactin in Non-Psychotic Organic Brain Syndrome of the Elderly", Exp Aging Res, 5(4): abstract only, 1979.

Gunn. "Relations Between Chemical Constitution, Pharmacological Actions, and Therapeutic Uses, in the Harmine Group of Alkaloids", From the Pharmacological Laboratory, University of Oxford:379-396, 1935.

Haber et al. "Tetrahydroisoquinolines—Endogenous Products After Chronic Alcohol Abuse", Pharmazie, 47/1: abstract only, 1992.

Halikas et al. "Treatment of Crack Cocaine Use with Carbamazepine", Am J Drug Alcohol Abuse, 18(1): abstract only, 1992.

Hanks. "Opioid-responsive and opioid-non-responsive pain in cancer", British Medical Bulletin 47:718-731, 1991.

Hardman et al. "Goodman & Gilman's The Parmacological Basis of Therapeutics" (9th ed, 1996) p. 51 and 57-58.

Harsing, Jr. et al. "Evidence that Ibogaine Releases Dopamine from the Cytoplasmic Pool in Isloated Mouse Striatum", Journal of Neural Transmission General Section, 96(3): abstract only, 1994.

Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.

Heel et al. "Buprenorphine: A Review of Its Pharmacological Properties and Therapeutic Efficacy", Drugs, 17(2): abstract only, 1979.

Henry et al. "Reversible Cerebral Arteriopathy Associated with the Administration of Ergot Derivatives", Cephalalgia, 4/3: abstract only, 1984.

Ho et al. "Metabolism of Harmaline in Rats." Biochemical Pharmacology, 20:1313-1319, 1971.

Hoes. "Clinical Criteria for the Selection of Anxiolytics", Tijdschr. Ther. Geneesm. Onderz., 9/9: abstract only, 1984.

Holbrook. "Nicotine Addiction." In Isselbacher et al. Harrison's Principles of Internal Medicine:2433-2437, 1994.

Holzner et al. "The Neuroleptic Sleeping Course in Chronic Headache", Therapiewoche, 35/36: abstract only, 1985.

Huang et al. "Cytotoxicity and Sister Chromatid Exchanges Induced in Vitro by Six Anticancer Drugs Developed in the People's Republic of China", J Natl Cancer Inst, 71(4): abstract only, 1983.

Hubens et al. "Chronic Intake of a Hydrogenated Ergot Alkaloid Causing Peripheral Vascular Ischemia—A Case Report", Vasc. Surg., 21/4: abstract only, 1987.

Huffman et al. "A Formal Synthesis of (±)-Ibogamine", J. Org. Chem. vol. 50, pp. 1460-1464, 1985.

Isler. "Treatment of Headache", Schweiz. Med. Wochenschr., 114/35: abstract only, 1984.

Jaffe. "Drug Addiction and Drug Abuse." In Gilman et al. Goodman and Gilman's The Pharmacological Basis of Therpeutics:522-523, 559-568, 1990.

Jaffe. "Psychopharmacology and Opiate Dependence", U.S. Public Health Serv. Publ., 1957-1967:1836, 1967.

James, "Linkers for solid phase organic synthesis", Tetrahedron 55, 4855-4946, 1999.

Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.

Jansen et al. "Ethnopharmacology of Kratom and the Mitragyna Alkaloids", J Ethnopharmacol, 23(1): abstract only, 1988.

Janzen. "History of Use of Psychotropic Drugs in Central Africa", Psychotropes, 1/2: abstract only, 1983.

Justins. "Management strategies for chronic pain", Annals of the Rheumatic Diseases, vol. 55, pp. 588-596, 1996.

Kalix. "Khat: A Plant with Amphetamine Effects", J Subst Abuse Treat, 5(3): abstract only, 1988.

Kalix. "Pharmacological Properties of the Stimulant Khat", Pharmacol. Ther., 48/3: abstract only, 1990.

Keefner. "A Gas Chromatography-Mass Spectrometry (GCMS) Method for Ibogaine", Society for Neuroscience Abstracts, 19(1-3): abstract only, 1993.

Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.

(56) References Cited

OTHER PUBLICATIONS

Knoll. "Azidomorphines and Homopyrimidazols: A New Approach to the Ideal Analgetic", Acta Physicol Pharmacol Bulg, 3(2): abstract only, 1977.
Knoll. "Azidomorphines: A New Family of Potent Analgesics with Low Dependence Capacity", Prog. Neuro-Psychopharmacol., 3/1-3: abstract only, 1979.
Koch et al. "Drug-Induced Liver Injury in Liver Biopsies of the Years 1981 and 1983, their Prevalence and Type of Presentation", Path. Res. Pract., 179: abstract only, 1985.
Konig. "Psychiatric Intensive Therapy After Acute Alkaloid Withdrawal Syndrome", Infusionsther Klin Ernahr, 6(1): abstract only, 1979.
Kornetsky, "Pharmacology Drugs Affecting Behavior", New York, John Wiley & Sons, pp. 186-187, 1976.
Kostowski et al. "The Effects of Some Hallucinogens on Aggressiveness of Mice and Rats" Pharmacology vol. 7, pp. 259-263, 1972.
Krug. "Cocaine Abuse: Historical, Epidemiologic, and Clinical Perspectives for Pediatricians", Advances in Pediatrics, 36:369-406, 1989.
Kupers et al., "Morphine differentially affects the sensory and affective pain ratings in neuorgenic and idiopathic forms of pain." Pain 47:5-12, 1991.
Lakoski et al. "Electrophysiologic Characterization of an Ibogaine Metabolite in Dorsal Raphe Nucleus and Hippocampus." Soc. Neurosc. 21:716 Abstract only, 1995.
Larson-Prior et al. "Electrophysiologic Characterization of an Ibogaine Metabolite in the Cerebellar Cortex." Soc. Neurosc. 21:716 Abstract only, 1995.
Lemontt et al. "Increase MDR Gene Expression and Decreased Drug Accumulation in Multidrug-Resistant Human Melanoma Cells", Cancer Res, 48(22): abstract only, 1988.
Leoni et al. "Effect of Cocaine and Morphine on Neutral Endopeptidase activity of Human Peripheral Blood Mononuclear Cells Cultures with Lectins", Cell Biochem Funct, 11(3): abstract only, 1993.
Lerida et al. "Incidence of Morphine Withdrawal and Quasi-Abstinence Syndrome in a Model of Chronic Pain in the Rat", Neurosci., 81(1-2): abstract only, 1987.
Lewis et al. "Adverse Reactions and Interactions with .beta.-Adrenoceptor Blocking Drugs", Med. Toxicol., 1/5: abstract only, 1986.
Lewis et al. "Narcotic Analgesics and Antagonists", Annu Rev Pharmacol, 11: abstract only, 1971.
Licht et al. "Induction of Multiple-Drug Resistance During Anti-Neoplastic Chemotherapy In-Vitro", Int J Cancer, 49(4): abstract only, 1991.
Ling et al., "Drugs of Abuse-Opiates", in Addtiction Medicine [Special Issue], Western Journal of Medicine, 152:565-572, 1990.
Low et al. "Effects of Acronycine and Cytouchalasin B on the Division of Rat Leukemia Cells", Exp Cell Res, 131(1): abstract only, 1981.
Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.
Maisonneuve et al. "Interactions of Ibogaine and D-Amphetamine: in vivio Microdialysis and Motor Behavior in Rats." Brain Research 579:87-92, 1992.
Maisonneuve et al. "Acute and Prolonged Effects of Ibogaine on Brain Dopamine Metabolism and Morphine-Induced Locomotor Activity in Rats", Brain Research, 575(1): abstract only, 1992.
Maisonneuve et al. "Interactions Between Ibogaine, a Potential Anti-Addictive Agent, and Morphine: an in Vivo Microdialysis Study", Eur. J. Pharmacol., 199(1): abstract only, 1991.
Martellotta et al. "Effects of the Calcium Antagonist Isradipine on Cocaine Intravenous Self-Administration in Rats", Psychopharmacologia, 113(3-4): Abstract only, 1994.
Martin et al. "Neuropathic Pain in Cancer Patients: Mechanisms, Syndromes, and Clinical Controversies," Journal of Pain and Symptom Management 14(2):99-117, 1997.

Mash et al, "Properties of Ibogaine and its Principle Metabolite (12-hydroxyibogamine) at the MK-801 binding site of the NMDA receptor complex," Neuroscience Letters, 192, 53-56, 1995.
Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.
Mash et al. "Preclinical screening of an ibogaie metabolite (noribogaine) on cocaine-induced hyperlocomotion and cocaine self-administration." Soc. Neurosc. 22:1929 Abstract only, 1996.
Mash et al. "Ibogaine in the Treatment of Heroin Withdrawal," The Alkaloids 56:1-17, 2001.
Mateer et al. "Reversible Ipecac Myopathy", Arch. Neurol., 42/2: abstract only, 1985.
Matharu et al. "Preformulation and Development of Ibogaine Injection for the Treatment of Drug Abuse", Pharmaceutical Research, 10: abstract only, 1993.
Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.
McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.
Melchior et al. "Preference for Alcohol Evoked by Tetra Hydro Papaveroline Chronically Infused in the Cerebral Ventricle of the Rat", Pharmacol Biochem Behav, 7(1): abstract only, 1977.
Mendelson et al. "Cocaine and Other Commonly Abused Drugs." In Isselbacher et al. Harrison's Principles of Internal Medicine:2429-2433, 1994.
Menzies et al. "Gangrene of the Small Bowel: A Complication of Methysergide Therapy", Aust. N. Z. J. Surg., 52/5: abstract only, 1982.
Metelitsa. "Pharmacological Agents in Controlling Smoking", Biull Vsesoiuznogo Kardiol Nauchn Tsentra, 10(1): abstract only, 1987.
Millan, "k-Opioid Receptors and Analgesia," Trendes in Pharmacologicla Sciences, 11, pp. 70-76, 1990.
Mizuhashi et al. "Antitumor Activities of IKP-104 A 4-1H Pyridizinone Derivative on Cultured and Implanted Tumors", Jpn J Cancer Res, 81(12): abstract only, 1990.
Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2): abstract only, 1989.
Mulamba et al., Alcaloides de Tabernanthe Pubescens. Journal of Natural Products, vol. 44, No. 2, p. 184-189, 1981.
Naranjo. "Ibogaine in psychotherapy: psychoanalysis according to Naranjo", part IV, pp. 1-2. http://www.nettuno.it/fiera/electric.italy/bwitif:html, 1996.
Nishiyama et al. "Expression of the Multidrug Transporter, P-Glycoproteiin, in Renal and Transitional Cell Carcinomas", Cancer, 71(11):3611-3619, 1993.
Nooter et al. "Multidrug Resistance (MDR) Genes in Haematological Malignancies", Cytotechnology, 12(1-3): abstract only, 1993.
Nunn-Thompson et al. "Pharmacotherapy for Making Cessation", Clin Pharm, 8(10): abstract only, 1989.
Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.
O'Hearn et al. "Degenration of Prukinje Cells in Parasagittal Zones of the Cerebellar Vermis After Treatment with Ibogaine of Harmaline", Neuroscience, 55(2): abstract only, 1993.
O'Hearn et al. "Ibogaine Induces Glial Activation in Parasagittal Zones of the Cerebellum", Neuroreport, 4/3: abstract only, 1993.
Pablo et al, "Noribogaine Stimulates Naloxone-Sensitive[35S]GTPgammaS Binding," NeuroReport, 9, pp. 109-114. (Website Publication Date of Dec. 20, 1997.), 1998.
Pacifici et al. "Immunological Effect of Cocaine and Host Resistance in Mice", Int J Immunother, 8(2): abstract only, 1992.

(56) References Cited

OTHER PUBLICATIONS

Palyi. "Survivial Responses to New Cytostatic Hexitols of P388 Mouse and K562 Leukemia Cells in Vitro", Cancer Treat. Rep., 70(2): abstract only, 1986.
Pantazis et al. "Efficacy of Camptothecin Congeners in the Treatment of Human Breast Carcinoma Xenografts", Oncology Research, 5(8): abstract only, 1994.
Pehek. "Effects of Cathinone and Amphetamine on the Neurochemistry of Dopamine in Vivo", Neuropharmacology, 29/12: abstract only, 1990.
Perera et al. "Tertiary Indole Alkaloids of Tabernaemontana Dichotoma Seeds", Planta Med., 49/1: abstract only, 1983.
Perrin. "Clinical Pharmacokinetics of Ergotamine in Migraine and Cluster Headache", Clin. Pharmacokin., 10/4: abstract only, 1985.
Popik et al. "NMDA Antagonist Properties of the pUtative Antiaddictive Drug, Ibogaine", Journal of Pharmaceutical and Experimental Therapeutics, 275(2), 753-760, 1995.
Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.
Popik et al. "100 Years of Ibogaine: Neurochemical and Pharmacological Actions of a Putative anti-addictive Drug", Pharmacological Reviews 47(2), pp. 235-253, 1995.
Pulvirenti et al. "Lisuride Reduces Intravenous Cocaine Self-Administration in Rats", Pharmacology, Biochemistry and Behavior, 47(4): abstract only, 1994.
Qiu et al. "The Influence of Chronic Nicotine Treatment on Stress-Induces Gastric Ulceration and Emptying Rate in Rats", Experientia, 48(4): abstract only, 1992.
Rezvani et al. "Noribogaine, a Primary Ibogaine Metabolite, Reduces Alcohol Intake in P and Fawn-Hooded Rats." RSA Annual Scientific Meeting Abstract only, 1995.
Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.
Ricceri et al. "Postnatal cocaine Esposure Affects Neonatal Passive Avoidance Performance and Cholinergic Development in Rats", Pharmacology, Biochemistry and Behavior, 45(2): abstract only, 1993.
Rodriguez et al. "Cocaine Adminstration Prior to Reactivation Facilitates Later Acquisition of an Avoidance Response in Rats", Psychopharmacologia, 112(2-3): abstract only, 1993.
Rosenmund et al. "Ibogamin, Ibogain and Epiibogamin" Chem. Ber. vol. 108, p. 1871-1895, 1975. structures and abstract only.
Sachs et al. "Corneal Complications Associated with the Use of Crack Cocaine", Ophthalmology, 100(2): abstract only, 1993.
Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.
Samadi-Baboli et al. "Preparation of Low Density Lipoprotein-9-Methoxy-Illipticin Complex and Its Cytotoxic Effect Against L1210 and P 388 Leukemic Cells in Vitro", Eur J Cancer Clin Oncol, 25(2): abstract only, 1989.
Saper et al. "Ergotamine Tartrate Dependency: Features and Possible Mechanisms", Clin. Neuropharmacol., 9/3: abstract only, 1986.
Schecter et al. "Comparison of the Behavioral Effects of Ibogaine from Three Sources: Mediation of Discriminative Activity", European Jornal of Pharmacology, 249(1): abstract only, 1993.
Schneider et al. "Analysis of the Cardiovascular Action of Ibogaine Hydrochloride (1)" Arch. Int. Pharmacodyn. vol. 110, pp. 92-102, 1957.
Schneider et al., "Neuropharmacological Studies of Ibogaine: An Indole Alkaloid with Central Stimulant Properties" Ann. of N.Y. Acad. Sci. vol. 66, pp. 765-776, 1957.
Schneider et al., "Potentiation Action of Ibogaine on Morphine Analgesia" Experiential vol. 12, pp. 323-324, 1956.
Schnider et al. "Use and Abuse of Analgesics in Tension-Type Headache", Cephalalgia, 14/2: abstract only, 1994.
Schuckit et al. "Opioid Drug Use." In Isselbacher et al. Harrison's Principles of Internal Medicine :2425-2429, 1994.
Schuckit. "Alcohol and Alcoholism." In Isselbacher et al. Harrison's Principles of Internal Medicine:2420-2425, 1994.
Seeber et al. "In Vivo Resistance Towards Anthracyclines, Etoposide, and Cis-Diamminedichloroplatinum (II)", Cancer Res., 42(11): abstract only, 1982.
Sehested et al. "The Carboxylic Ionophore Monensin Inhibits Active Drug Efflux and Modulates In-Vitro Resistance in Daunorubicin Resistant Enrlich Ascites Tumor Cells", Biochem Pharmacol, 37(17): abstract only, 1988.
Sershen et al. "Ibogaine Antagonizes Cocaine-Induced Locomotor Stimulation in Mice", Life Sci., 50(15): abstract only, 1992.
Sershen et al. "Ibogaine Reduces Amphetamine-Induced Locomotor Stimulation in C57BL/6By Mice, but Stimulates Locomotor Activity in Rats", Life Sci., 51(13): abstract only, 1992.
Sershen et al. "Ibogaine Reduces Preference for Cocaine Consumption in C57BL/6By Mice", Pharmacol., Biochem. Behay., 47(1): abstract only, 1994.
Shen et al. "Antagonists at Excitatory Opioid Recepta on Sensory Neurons in Culture Increase Potency and Specificity of Opiate Analgesics and Attenuate Development of Tolerance / Dependence", Brain Research, 636(2): abstract only, 1994.
Sheppard. "A Preliminary Investigation of Ibogaine: Case Reports and Recommendations for Further Study", J. Subst. Abuse Treat., 11/4: abstract only, 1994.
Shir et al., "Neuropathic pain unrelieved by morphine, alleviated by haloperidol" Harefuah 118(8):452-454, Abstract only, 1990.
Shook et al. "A cyclic Somatostatin Analog that Precipitates Withdrawal in Morphine-Dependent Mice", NIDA Res. Monogr., 76(Probl. Drug Depend.): abstract only, 1987.
Sinkula et al. "Rationale for Design for Biologically Reversible Drug Derivatives: Prodrugs." Journal of Pharmaceutical Sciences, 64(2):181-210, 1975.
Slotkin et al. "A Model of Harmine Metabolism in the Rat." The Journal of Pharmacology and Experimental Therapeutics, 174(3):456-462, 1970.
Slotkin et al. "Blood Levels and Urinary Excretion of Harmine and its Metabolites in Man and Rats." The Journal of Pharmacology and Experimental Therapeutics, 173(1):26-30, 1970.
Slotkin et al. "Urinary Metabolites of Harmine in the Rat and their Inhibition of Monoamine Oxidase." Biochemical Pharmacology 19:125-131, 1970.
Sloviter et al. "A Common Mechanism of Lysergic Acid, Indolealkylamine and Phenethylamine Hallucinogens: Serotonergic Mediation of Behavioral Effects in Rats" J. Pharm. Exp. Ther. vol. 214, No. 2, pp. 231-238, 1980.
Smith. "Interaction of Biogenic Amines with Ethanol", Adv Exp Med Biol, 56: abstract only, 1975.
Solinas et al. "Solid-supported reagents and catch-and-release techniques in organic synthesis". Synthesis Aug. 16, 2007 DE LNKD-DOI:10.1055/S-2007-983806, No. 16., pp. 2409-2453, 2007.
Stella. "Pro-drugs: An Overview and Definition." Prodrugs as Novel Drug Delivery System. ACS Symposium Series :1-115, 1975.
Stella. "Pro-drugs as Novel Drug Delivery Systems", Higuchi, T. et al., ed. (American Chemical Society, Washington), pp. 1-49, 1975.
Sugiyama et al. "Quantitative Analysis of Cell-Kill Effects of Anticancer Drugs: Consideration of Both In Vitro and In Vivo Expreimental Systems", Gan to Kagaku Ryoho, 14(12): abstract only, 1987.
Tarnower et al. "Ergotism Masquerading as Arteritis", Postgrad Med, 85(1): abstract only, 1989.
Teoh et al. "Buprenorphine Effects on Morphine- and Cocaine-Induced Subjective Responses by Drug—Dependent Men", Journal of Clinical Psychopharmacology, 14(1): abstract only, 1994.
Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.
Torrenegra et al. "Alkaloids of stemmadenia grandiflora", Phytochemistry, 27(6): pp. 1843-1848, 1988.
Tsuruo. "Multidrug Resistance: A Transport System of Antitumor Agents and Xenobiotics", Princess Takamatsu Symp, 21: abstract only, 1990.

(56) References Cited

OTHER PUBLICATIONS

Uldry et al. "Cerebrovascular Accidents in Relation to Drug Consumption or Drug Abuse", Schweiz Rundsch Med Prax, 78(23): abstract only, 1989.

Valadez et al. "Persistence of the Ability of Amphetamine Preexposure to Facilitate Acquistion of Cocaine Self-Administration", Pharmacology, Biochemistry and Behavior, 47(1): abstract only, 1994.

Valencia et al. "Obovatine, a new bisindole alkaloid from stemmadenia obovata", Journal of Natural Products, 58(1):pp. 134-137, 1995.

Vescovi et al. "Successful Treatment of Opiate Withdrawal Using Lysine Acetylsalicylate", Curr. Ther. Res., Clin. Exp., 33/5: abstract only, 1983.

Villalba et al. "Uses and Abuses of Ipecacuana Syrup", Farm. Clin., 9/1: abstract only, 1992.

Wells et al. "Recognition and Treatment of Arterial Insufficiency from Cafergot", J. Vasc. Surg., 4/1: abstract only, 1986.

Whitaker et al. "High Affinity 3H-Serotonin Binding to Caudate: Inhibition by Hallucinogenic and Serotonergic Drugs", Psychopharmacology, vol. 59, pp. 1-5, 1978.

Whitaker et al., "Selective Labeling of Serotonin Receptors d'(3H)Lysergic Acid Diethylamide in Calf Caudate", Proc. Natl. Acad. Sci., USA vol. 75, No. 12, pp. 5783-5787, 1978.

Whittaker et al. "Recurrent Laryngeal Nerve Paralysis in Patients Receiving Vincristine and Vinblastine", Br Med J, 1(6071): abstract only, 1977.

Widler et al. "Pharmacodynamics and Pharmacokinetics of Khat: a Controlled Study", Clin. Pharmacol. Ther., 55/5: abstract only, 1994.

Wildmann. "Heterocycles as Physiological Ligands for the Benzodiazepine Receptor and for Other Binding Sites", Pharmacol Res, 21(6): abstract only, 1989.

Williams, Jr. et al. "The 'Alice in Wonderland' Experience Ergot Alkaloid Therapy for Prolactin-Secreting Pituitary Tumors", West. J. Med., 138/3: abstract only, 1983.

Wishart et al. "Is Multidrug Resistance Relevant in Breast Cancer", Eur. J. Surg. Oncol., 17/5: abstract only, 1991.

Witt et al. "Pharmacodynamic and Pharmacokinetic Characterization of Poly(Ethylene glycol) Conjugation to Met-Enkephalin Analog [$_D$-Pen$^2$,$_D$-Pen$^5$]-enkephalin (DPDPE)", J. of Pharm. and Exp. Thera., 298(2), pp. 848-856, 2001.

Witt et al. "Pluronic P85 Block Copolymer Enhances Opioid Pepetide Analgesia", J. of Pharm. and Exp. Thera., 303(2), pp. 760-767, 2002.

Worz. "Effects and Risks of Psychotropic and Analgesic Combinations", Am. J. Med., 75/5A: abstract only, 1983.

Zetler et al. "Pharmacokinetics in the Rat of the Hallucinogenic Alkaloids Harmine and Harmaline." Naunyn-Schmiedeberg's Arch. Pharmacol., 285, 273-292, 1974.

Zetler et al. "Cerebral Pharmacokinetics of Tremor-Producing Harmala and Iboga Alkaloids" Pharmacology vol. 7, No. 4, pp. 237-248, 1972.

Database Registry Chemical Abstracts Service, Columbus, Ohio, US; 1984, "Ibogamine-18-carboxylic acid, 12-methoxy-, potassium sal", Database accession No. 5500-12-9.

Greenwald, et al., "Poly(ethylene glycol) conjugated drugs and prodrugs: a comprehensive review," Crit. Rev. Ther. Drug Carrier Syst., (2000), 17(2):101-161.

International Search Report and Written Opinion dated Mar. 11, 2013 in related PCT Patent Application No. PCT/US2012/071052.

International Search Report and Written Opinion dated Oct. 4, 2012 in related PCT Patent Application No. PCT/US2012/022255.

International Search Report and Written Opinion dated Oct. 4, 2011 for related PCT Patent Application No. PCT/US2011/045081.

Layer, et al., "Structurally modified ibogaine analogs exhibit differing affinities for NMDA receptors," European Journal of Pharmacology, (1996), 309:159-165.

Siew, Koon T. et al. "Buprenorphine Effects on Morphine- and Cocaine- Induced Subjective Responses by Drug—Dependent Men", Journal of Clinical Psychopharmacology, 14(1): abstract only, 1994.

Yang, et al., "Prodrug based optimal drug delivery via membrane transporter/receptor," Expert. Opin. Biol. Ther., (2001), 1(2):159-175.

Snyder, et al., (1997). "Practical HPLC Method Development". pp. 214-218, 266, 267, 282 & 283 Wiley.

Stahl, et. al., (1998) "Handbook of Pharmaceutical Salts". John Wiley & Sons, p. 250.

First Office Action for Chinese Appl. No. 201180038173.7, dated Mar. 25, 2014.

Niemann et al, "The Isolation of Rupicoline and Montanine, Two Pseudoindoxyl Alkaloids of Tabernaemontana Rupicola Benth", The Journal of Organic Chemistry, 31(7):2265-2269, 1966.

METHODS AND COMPOSITIONS FOR PREPARING NORIBOGAINE FROM VOACANGINE

FIELD OF THE INVENTION

This invention relates generally to methods and compositions for preparing and purifying the non-addictive alkaloid noribogaine.

STATE OF THE ART

Noribogaine is a well known member of the ibogaine family of alkaloids and is sometimes referred to as 12-hydroxyibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tryptamine, tetrahydrohavaine and indolazepines. Noribogaine can be depicted by the following formula:

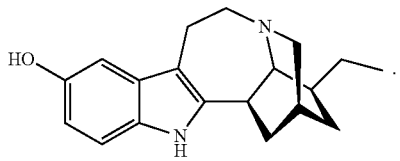

Noribogaine and its pharmaceutically acceptable salts have recently received significant attention as a non-addictive alkaloid useful in treating drug dependency (U.S. Pat. No. 6,348,456) and as a potent analgesic (U.S. Pat. No. 7,220,737).

Conventionally, noribogaine is prepared by demethylation of naturally occurring ibogaine:

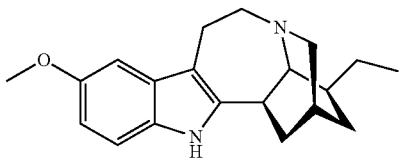

which is isolated from *Tabernanth iboga*, a shrub of West Africa. Demethylation may be accomplished by conventional techniques such as by reaction with boron tribromide/methylene chloride at room temperature followed by conventional purification. Alternatively, noribogaine can be prepared from the naturally occurring alkaloid, voacangine

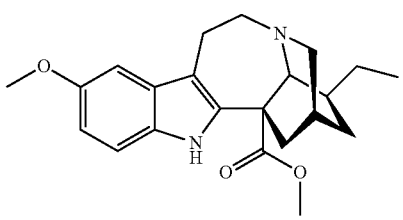

by decarboxylation followed by demethylation as described in U.S. Pat. No. 2,813,873. Such a process provides for ibogaine as the first intermediate in this two step synthesis.

Ibogaine is addictive and possesses hallucinogenic properties. It is a Schedule 1-controlled substance as provided by the US Food and Drug Administration. Accordingly, methods for preparing noribogaine from ibogaine require high levels of assurance that contamination with unacceptable levels of ibogaine is avoided. As above, a one-step method for preparation of noribogaine from ibogaine via demethylation does not provide the requisite assurance that ibogaine will consistently be removed as a potential contaminant. This applies equally as well to noribogaine prepared from voacangine as described above as the penultimate compound in this synthesis is ibogaine.

Accordingly, there is an ongoing need to provide a method for preparing noribogaine from voacangine such that the potential for ibogaine contamination can be effectively and reliably minimized.

SUMMARY OF THE INVENTION

This invention provides methods and compositions for the preparation of noribogaine wherein contamination by ibogaine is predictably and effectively minimized, if not altogether eliminated. In certain embodiments, this invention employs the use of solid supports to effect separation of noribogaine from any possible contaminants such that any ibogaine contamination is significantly reduced if not altogether eliminated. In certain embodiments, this invention employs an ion exchange resin to effect separation of noribogaine from any possible contaminants such that any ibogaine contamination is significantly reduced if not altogether eliminated.

Accordingly, in one of its method aspects, this invention is directed to a method for preparing noribogaine which method comprises:

a) converting voacangine to 12-hydroxyibogamine-18-carboxylic acid or the carboxylic acid salt or ester thereof, wherein the indole nitrogen is optionally protected by an amino protecting group;

b) optionally isolating the 12-hydroxyibogamine-18-carboxylic acid or the carboxylic acid salt, ester and/or amino protected derivative thereof;

c) converting the product of step a) or b) to noribogaine; and d) isolating noribogaine.

In another of its method aspects, this invention is directed to a method for preparing noribogaine which method comprises:

a) converting voacangine to 12-methoxyibogamine-18-carboxylic acid or the carboxylic acid salt or ester thereof, wherein the indole nitrogen is optionally protected by an amino protecting group;

b) optionally isolating the 12-methoxyibogamine-18-carboxylic acid or the carboxylic acid salt, ester and/or amino protected derivative thereof;

c) converting the product of step a) or b) to noribogaine; and d) isolating noribogaine.

In another of its method aspects, this invention is directed to a method for preparing noribogaine which method comprises:

a) converting voacangine to 12-hydroxyibogamine-18-carboxylic acid the carboxylic acid salt thereof, wherein the indole nitrogen is optionally protected by an amino protecting group;

b) converting the 12-hydroxyibogamine-18-carboxylic acid or the carboxylic acid salt and/or amino protected derivative thereof to noribogaine; and c) isolating noribogaine.

In another of its method aspects, this invention is directed to a method for preparing and purifying noribogaine which method comprises:
  a) converting voacangine to 12-hydroxyibogamine-18-carboxylic acid methyl ester wherein the indole nitrogen is optionally protected by an amino protecting group;
  b) optionally covalently attaching 12-hydroxyibogamine-18-carboxylic acid methyl ester or amino protected derivative thereof to a solid support via the hydroxyl group of 12-hydroxyibogamine-18-carboxylic acid methyl ester or amino protected derivative thereof so as to form a suspension of solid supports having 12-hydroxyibogamine-18-carboxylic acid methyl ester or amino protected derivative thereof bound thereto;
  c) removing residual voacangine from said suspension;
  d) cleaving and recovering the 12-hydroxyibogamine-18-carboxylic acid methyl ester or amino protected derivative thereof from the solid support;
  e) converting the 12-hydroxyibogamine-18-carboxylic acid methyl ester or amino protected derivative thereof to noribogaine; and
  f) isolating noribogaine.

In another of its method aspects, this invention is directed to a method for preparing and purifying noribogaine which method comprises:
  a) covalently attaching voacangine to a solid support via the indole nitrogen of voacangine so as to form a suspension of solid supports having voacangine bound thereto;
  b) converting voacangine to 12-hydroxyibogamine-18-carboxylic acid methyl ester or 12-hydroxyibogamine-18-carboxylic acid or carboxylic acid salt thereof under conditions wherein the level of voacangine bound to the solid support is less than 0.1 weight percent;
  c) cleaving and recovering 12-hydroxyibogamine-18-carboxylic acid methyl ester or 12-hydroxyibogamine-18-carboxylic acid or carboxylic acid salt thereof from the solid support;
  d) converting the 12-hydroxyibogamine-18-carboxylic acid methyl ester or 12-hydroxyibogamine-18-carboxylic acid or carboxylic acid salt thereof to noribogaine; and
  e) purifying noribogaine.

In another of its method aspects, this invention is directed to a method for preparing and purifying noribogaine which method comprises utilizing an ion exchange resin for isolating and/or purifying the 12-hydroxyibogamine-18-carboxylic acid methyl ester, 12-hydroxyibogamine-18-carboxylic acid or carboxylic acid salt thereof, or noribogaine or a corresponding salt thereof.

In one of its composition aspects, this invention is directed to a solid support having voacangine, 12-hydroxyibogamine-18-carboxylic acid methyl ester or 12-hydroxyibogamine-18-carboxylic acid or carboxylic acid salt thereof covalently bound thereto through a cleavable linker.

DETAILED DESCRIPTION OF THE INVENTION

This invention is directed to methods and compositions comprising noribogaine and, in particular, methods and compositions comprising highly pure noribogaine. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of such excipients.

1. Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As stated above, the invention is directed to compositions comprising noribogaine and an excipient to facilitate transport across the blood brain barrier.

As used herein, the term "noribogaine" refers to the compound:

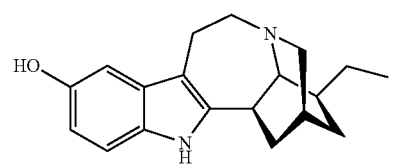

as well as its pharmaceutically acceptable salts thereof. Conventionally, noribogaine is prepared by demethylation of naturally occurring ibogaine:

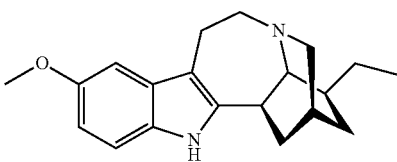

which is isolated from *Tabernanth iboga*, a shrub of West Africa. Demethylation may be accomplished by conventional techniques such as by reaction with boron tribromide/methylene chloride at room temperature followed by conventional purification. As disclosed herein, it is contemplated that noribogaine can be prepared essentially free of any potential ibogaine contamination from voacangine:

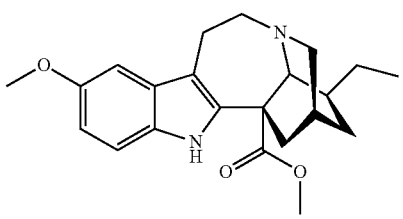

This invention is not limited to any particular chemical form of noribogaine and the drug may be given to patients either as a free base or as a pharmaceutically acceptable addition salt.

The term "12-hydroxyibogamine-18-carboxylic acid" refers to compounds of the formula:

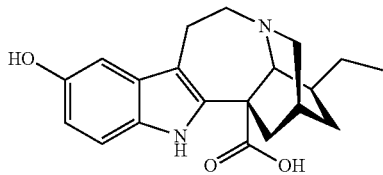

The term "carboxylic acid salt" refers to salts of the carboxylic acid moiety of 12-hydroxyibogamine-18-carboxylic acid. Exemplary salts include, but are not limited to, the lithium, sodium, and potassium salts.

The term "ester" refers to esters of the carboxylic acid moiety of 12-hydroxyibogamine-18-carboxylic acid having from 1 to 12 carbon atoms. Exemplary esters include, but are not limited to, methyl, allyl, benzyl, and aryl esters, as well as suitable substituted derivatives thereof.

The term "solid support" refers to a material having a rigid or semi-rigid surface which contain or can be derivatized to contain reactive functionality which covalently links noribogaine or ibogaine to the surface thereof through a cleavable linker. Such materials are well known in the art and include, by way of example, silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol, and the like.

As used herein, the term "cleavable linking arms" refer to linking arms, which are a chemical group or a covalent bond which covalently attaches at one end to a solid support and at the other end to ibogaine or noribogaine. At least one of the covalent bonds of the linking arm which attaches ibogaine or noribogaine to the solid support can be readily broken by specific chemical or enzymatic reactions, thereby providing for ibogaine or noribogaine free of the solid support. The chemical or enzymatic reactions employed to break the covalent bond of the linking arm are selected so as to be specific for bond breakage thereby preventing unintended reactions occurring elsewhere on the compound. The cleavable linking group is selected relative to ibogaine/noribogaine formed on the solid support so as to prevent premature cleavage of either ibogaine or noribogaine from the solid support as well as not to interfere with any of the procedures employed during synthesis on the support. Suitable cleavable linking arms are well known in the art, and may include such groups as carbonate groups, carbamate groups, amide groups, and the like. In a preferred embodiment, the cleavable linker arm contains no more than 10 atoms. More preferably, the cleavable linker contains from 1 to 4 carbon atoms and from 2 to 4 heteroatoms selected from oxygen, nitrogen, sulfur, S(O) and S(O)$_2$.

As used herein, the term "pharmaceutically acceptable salt" refers to pharmaceutically acceptable salts of noribogine which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

As used herein, the term "protecting group" or "Pg" refers to well known functional groups which, when bound to a functional group, render the resulting protected functional group inert to the reaction conditions to be conducted on other portions of the compound and which, at the appropriate time, can be reacted to regenerate the original functionality. The identity of the protecting group is not critical and is selected to be compatible with the remainder of the molecule. In one embodiment, the protecting group is an "amino protecting group" which protects the amino functionality of ibogaine or noribogaine during the reactions described herein. Examples of conventional amino protecting groups include, for instance, benzyl, acetyl, oxyacetyl, carboxybenzyl (Cbz), and the like. In another embodiment, the protecting group is a "hydroxy protecting group" which protects the hydroxyl functionality of noribogaine. Examples of hydroxyl protecting groups include, for instance, tosyl, benzyl, p-methoxybenzyl, p-nitrobenzyl, allyl, trityl, dialkylsilylethers, such as trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl, methoxymethyl and tosyl. Additional examples of hydroxy protecting groups may be found in standard reference works such as Greene and Wuts, Protective Groups in Organic Synthesis, 2d Ed., 1991, John Wiley & Sons, and McOmie Protective Groups in Organic Chemistry, 1975, Plenum Press.

Preparation and Purification of Noribogaine

Voacangine (12-methoxyibogamine-18-carboxylic acid methyl ester) is an alkaloid found predominantly in the root-bark of the *Voacanga africana* tree, as well as in other plants such as *Tabernanthe iboga*, *Tabernaemontana africana*, *Trachelospermum jasminoides* and *Ervatamia yunnanensis*. Voacangine has been previously used as a precursor for the semi-synthesis of ibogaine (see U.S. Pat. No. 2,813,873).

The present application contemplates methods for preparing noribogaine from voacangine without providing ibogaine as an intermediate. Such methods are useful for a number of reasons. First, the known methods for the preparation of noribogaine comprise demethylating ibogaine as the final step. This is unlikely to provide pure noribogaine, and ibogaine contamination is undesirable as it is a schedule 1 controlled substance and is known to induce severe hallucinations. Second, ibogaine is isolated from the root of the *Tabernanthe iboga* and is therefore only a semi-renewable source as the plant must be compromised for isolation to take place, whereas voacangine is isolated from the bark and is thus renewable.

The compounds of this invention can be prepared using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are iodocyclohexane in refluxing DMF, and the like. In some embodiments, the O-demethylation should be performed without converting the methyl ester to the corresponding carboxylic acid and/or without affecting the linkage to the solid support. Suitable reagents can be readily ascertained by one of skill in the art and can be found, for example, in T. W. Greene and G. M. Wuts, Protecting Groups in Organic Synthesis, Fourth Edition, Wiley, N.Y., 2007 (see, e.g., the reactivity charts at pages 1006-1008 and 1022-1032), and references cited therein.

Noribogaine 3 can be prepared and purified from voacangine 1 by any one of the routes shown in Scheme 1.

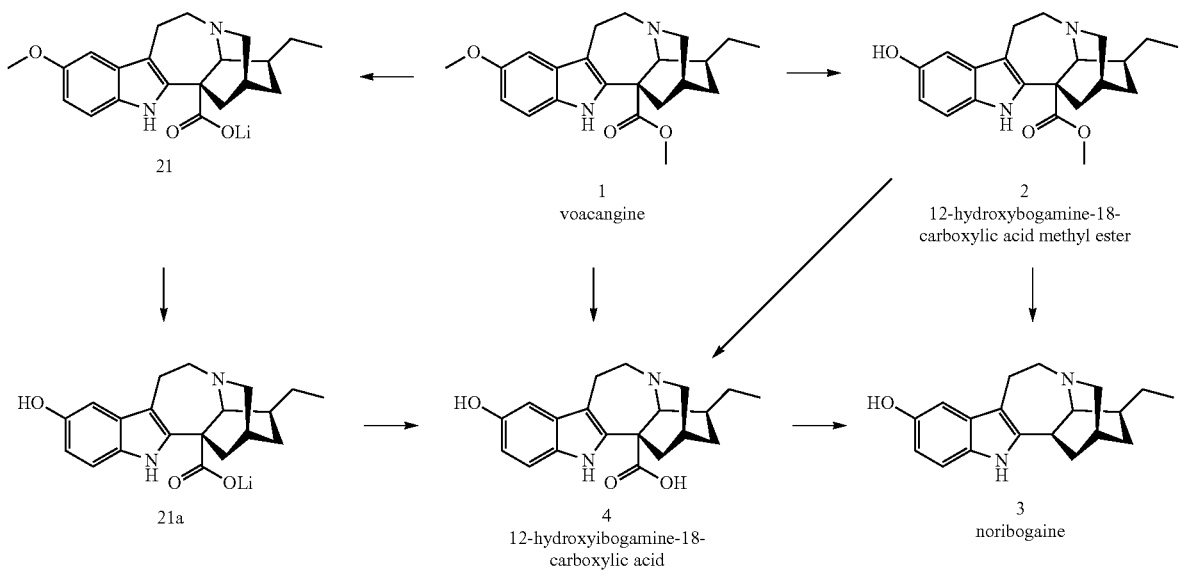

described in T. W. Greene and G. M. Wuts, Protecting Groups in Organic Synthesis, Fourth Edition, Wiley, N.Y., 2007, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

It is contemplated that noribogaine can be prepared and/or purified from ibogaine by utilizing solid support as shown in the following Schemes, where PG represents an amine protecting group, LG represents a leaving group (e.g. a halo or alcohol), L represents a cleavable linking group (e.g. a carbonyl compound such as a carbonate or carbamate) and the shaded circle represents a solid support. In the following Schemes, the O-demethylation of the aryl methoxy group to provide the corresponding phenol can be accomplishing using any suitable method known in the art. Suitable reagents include protic acids such as HBr and HCl, a Lewis acid (e.g. $BBr_3$, $BCl_3$, $BF_3$, $AlCl_3$, etc.), a nucleophile (e.g. RS—, $N_3$—, $LiPPh_2$, SCN—), NaCN at low pH (e.g. pH 12), as well as L-Selectride, $NaN(SiMe_3)_2$, $LiN(^iPr)_2$, $SnO_2$, TMSI, In one embodiment, provided herein is a method for preparing noribogaine 3, which method comprises demethylating the 12-methoxy functionality of voacangine 1 to provide the corresponding 12-hydroxyibogamine-18-carboxylic acid methyl ester 2, or the salt or ester thereof. In some embodiments, the indole nitrogen can be optionally protected by an amino protecting group, such as tert-butoxycarbonyl or para-methoxy benzyl. The demethylation of the 12-methoxy functionality to provide the corresponding phenol can be accomplishing using any suitable method known in the art, including, but not limited to, protic acids such as HBr and HCl, a Lewis acid (e.g. $BBr_3$, $BCl_3$, $BF_3$, $AlCl_3$, etc.), a nucleophile (e.g. $LiPPh_2$, RS—, $N_3$—, SCN—), NaCN at low pH (e.g. pH 12), as well as L-Selectride, $NaN(SiMe_3)_2$, $LiN(^iPr)_2$, $SnO_2$, TMSI, iodocyclohexane in refluxing DMF, and the like. Subsequent de-esterification of the methyl ester (typically under basic conditions) followed by decarboxylation provides noribogaine. These steps can be performed in the same pot, or if desired, in two separate steps to facilitate purification.

Under certain demethylation conditions, it may be the case that the methyl ester of the 12-hydroxyibogamine-18-carboxylic acid methyl ester 2 is hydrolyzed, thus forming the carboxylic acid (i.e., 12-hydroxyibogamine-18-carboxylic acid 4). In the event that the methyl ester of 2 is hydrolyzed to give 4, one of skill in the art could re-esterify 4 to provide the corresponding ester under conventional conditions. Alternatively, if the methyl ester is retained one can perform traditional transesterification procedure to arrive at a specific ester.

Exemplary esters include, but are not limited to, methyl, allyl, benzyl, and aryl esters, as well as suitable substituted derivatives thereof.

In the methods disclosed above, the demethylation of the 12-methoxy functionality of voacangine 1 should proceed without decarboxylation. Therefore, in certain embodiments, it may be that an acid scavenger is used. Such acid scavengers should not interfere with the demethylation reaction (e.g., they should not tie up the Lewis acid, etc.). Exemplary acid scavengers which could be used in the demethylation reaction include, but are not limited to, benzimidazole, 1,8-bis(dimethylamino)naphthalene, 1,8-bis(hexamethyltriaminophosphazenyl)naphthalene, other proton sponges, and the like.

The decarboxylation reaction can be facilitated with the use of a suitable reagent under standard reaction conditions known in the art. For example, decarboxylation can be performed using a protic acid (e.g., HBr, HCl, etc.), under radical conditions via the Barton ester using, e.g., tributyltin hydride or tert-butylmercaptan, optionally in the presence of a suitable radical trapping agent, or other methods such as the Hunsdiecker reaction using bromine via the silver(I) salt of the carboxylic acid. Other suitable methods will be apparent to one of skill in the art.

In some embodiments, the methyl ester and the 12-methoxy functionality of voacangine can be simultaneously demethylated to provide 12-hydroxyibogamine-18-carboxylic acid 4 in one step, and then subsequently decarboxylating the 12-hydroxyibogamine-18-carboxylic acid to provide noribogaine.

In some embodiments, the lithium salt of voacangine (21) can be prepared by treating voacangine (1) with n-butyllithium in hexane at 0° C. with 1-propanethiol (see, Kuehne, et al. *J. Med. Chem.,* 2003, 46, 2716-2730). The carboxylate anion and the lithium of 21 form a tight ion pair and thus compound 21 can be isolated and purified. The lithium salt of voacangine (21) can likewise be demethylated using, e.g., $BCl_3$ or $BBr_3$ in DCM, to provide compound 21a, which can then undergo decarboxylation under standard conditions, such as e.g., acid catalyzed decarboxylation using HBr or HCl, to provide the appropriate salt of noribogaine 3. Both compounds 21 and 21a can be isolated and purified as compounds per se. The noribogaine can be isolated as the fee base or a salt thereof, such as the hydrochloride or hydrobromide salt thereof. In one embodiment, the noribogaine is isolated as noribogaine hydrochloride. In another embodiment, the noribogaine is isolated as noribogaine hydrobromide. One of skill in the art could readily interchange the anion using conventional methods.

Purification

Noribogaine 3, as well as the various intermediates disclosed herein can be further purified using standard techniques known in the art, such as column chromatography, crystallization, solid support chemistry, ion exchange chromatography, and the like.

Noribogaine 3, as well as intermediates 2 and 4 (as prepared in Scheme 1) can be purified using solid support chemistry as shown in Scheme 2.

Scheme 2

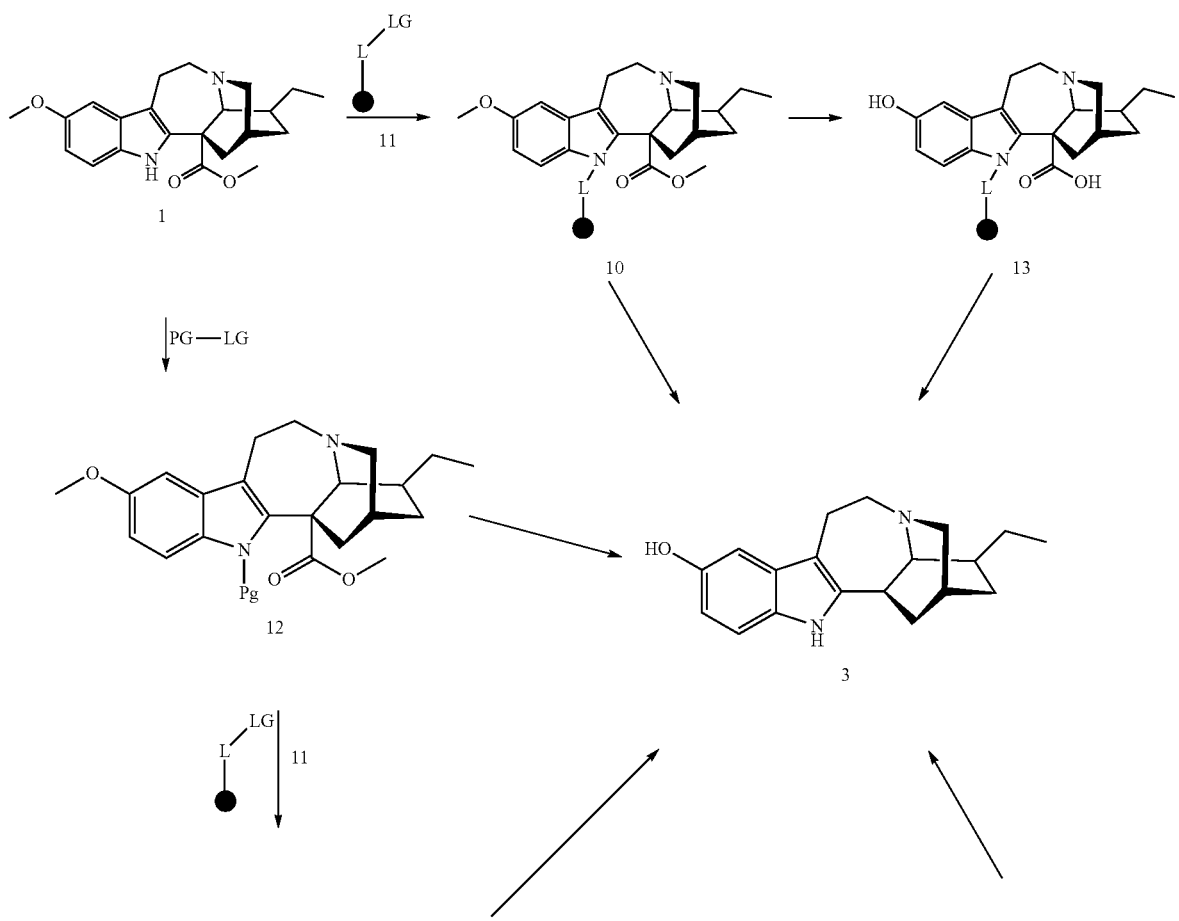

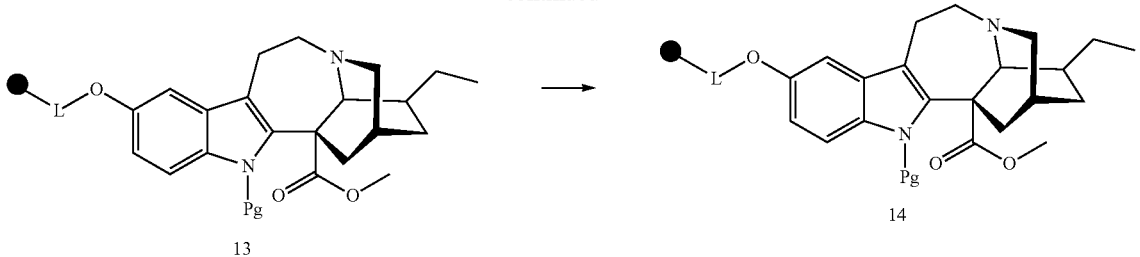

In one embodiment, the indole amine of voacangine 1 can be protected using an amine protecting group (PG-LG) to provide compound 12, followed by either tandem demethylation/decarboxylation followed by removal of the amine protecting group, or sequential demethylation (intermediates 12 and 13), followed by de-esterification and decarboxylation and removal of the amine protecting group to provide noribogaine 3. In addition, in one embodiment, noribogaine 3 can be directly prepared and purified from the demethylation/decarboxylation of voacangine 1 using methods known in the art and then purified by appending noribogaine to a solid support (compound 14), washing any contaminants, cleaving the linking group L, and recovering the noribogaine 5. In the above syntheses, one or more of the noribogaine or intermediates shown above can be purified using standard purification techniques known in the art (e.g. column chromatography, ion exchange chromatography, HPLC, and the like). Compounds of formula 11 are commercially available or can be synthesized in one or two steps from commercially available starting materials (see, e.g. commercially available resins from Sigma-Aldrich®). In the compounds of Scheme 2, the linking group, L, contains a cleavable bond which is not susceptible to cleavage under the demethylating conditions used (e.g., BBr$_3$).

In one embodiment, noribogaine can be prepared and purified using solid support chemistry known in the art starting from N-protected voacangine 12 in the manner shown in Scheme 3 below, wherein Pg is hydrogen or an amino protecting group and the shaded circle represents a solid support.

Scheme 3

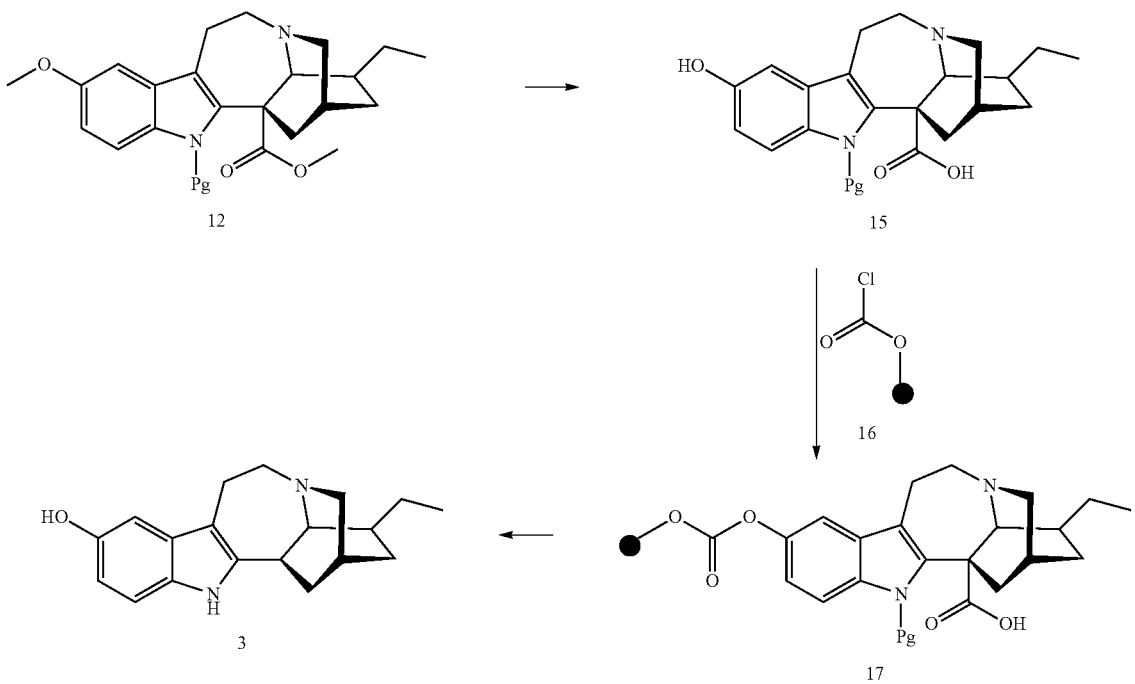

Specifically, in Scheme 3, N-protected voacangine 12, can be contacted with boron tribromide in methylene chloride using conditions well known in the art to provide compound 15. Attachment of N-protected voacangine 12 to a solid support can be accomplished by use of a chloroformate/solid support, compound 16, under conventional conditions to provide for compound 17 wherein the carbonate group is shown for illustrative purposes only as the cleavable linking group. Other cleavable linkers can likewise be used in the methods depicted in Scheme 3. As compound 12 does not contain a functional group reactive with compound 3, only compound 15, will react with the solid support and provide for compound 17. Repeated washing of compound 17 will remove any unreacted compound 12 from contaminating the sample of amino protected noribogaine used in this reaction. Furthermore, at any time, a small portion of the solid support can be removed to provide a sample of noribogaine 3 (after cleavage of the solid support and N-deprotection/decarboxylation). The sample can then be analyzed for purity by conventional methods such as GC/LCMS, HPLC, NMR, etc.

As desired, exceptionally pure noribogaine 3 can be obtained by repeating the process of binding compound 3 to a solid support via the hydroxyl group of amino protected noribogaine and washing any contaminating voacangine from the suspension. By repeating this process as often as necessary and preferably no more than 5 times, it is contemplated that noribogaine 3 having no detectable amount of ibogaine (i.e. less than 100 ppt) can be prepared.

In another embodiment, noribogaine can be prepared and purified from voacangine 1 in the manner described in Scheme 4 below.

interact with oppositely charged groups of the compound to be retained. Such methods are utilized routinely in the art to purify compounds having an ionic functional group, such as an ionized phenol. Accordingly, a solution containing 2, 3, or 4, or an anion thereof, can be loaded onto a suitable cationic resin. Any residual unreacted ibogaine present can then be eluted using a suitable solvent (e.g., acetone, ethyl acetate, etc.). Once the eluent is determined to be free of ibogaine (e.g., by HPLC, LCMS, etc.), the purified 2, 3, or 4 can be eluted off the resin. Suitable cationic resins can be purchased from commercial sources (Aldrich®, Fisher Scientific®, etc.).

The following synthetic and biological examples are offered to illustrate this invention and are not to be construed in any way as limiting the scope of this invention. Unless otherwise stated, all temperatures are in degrees Celsius.

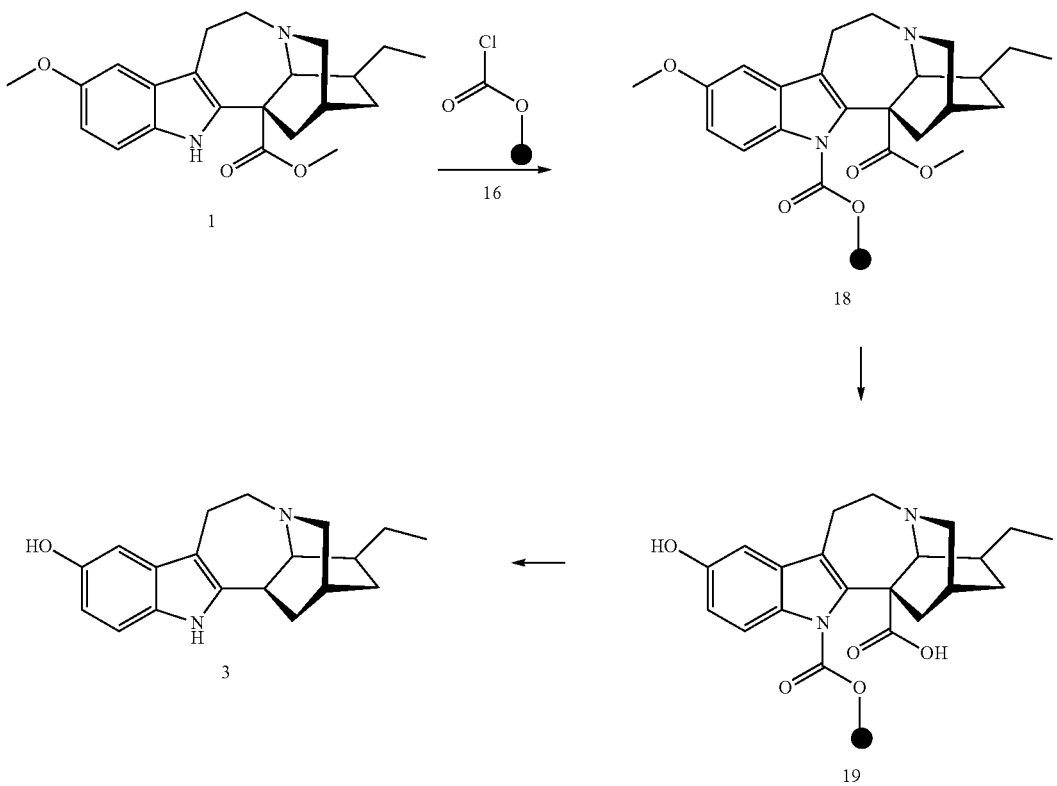

Scheme 4

In Scheme 4, voacangine 1 can be bound via conventional techniques to a solid support, compound 16, through a cleavable linker arm which, for the sake of illustration only, is depicted as a carbamate bond in resulting compound 18. Compound 18 can then be contacted with boron tribromide in methylene chloride using conditions well known in the art to provide for compound 19. Cleavage of the cleavable linker in compound 19 provides for noribogaine 3.

In one embodiment, noribogaine 3 can be purified by conventional techniques including high performance liquid chromatography (HPLC) and the purity level of the resulting purified compound confirmed by GC/LCMS. In addition, the noribogaine and any of the intermediates (i.e., either of compounds 2 or 4) can be further purified using ion exchange chromatography. In principal, the stationary phase is an ion exchange resin that carries charged functional groups which

EXAMPLES

In the examples below, the following abbreviations have the following meanings. If an abbreviation is not defined, it has its generally accepted meaning.

Example 1

Synthesis of Noribogaine from Voacangine

Example 1 illustrates one method for the synthesis and purification of noribogaine from ibogaine which method follows Scheme 5 below.

Scheme 5

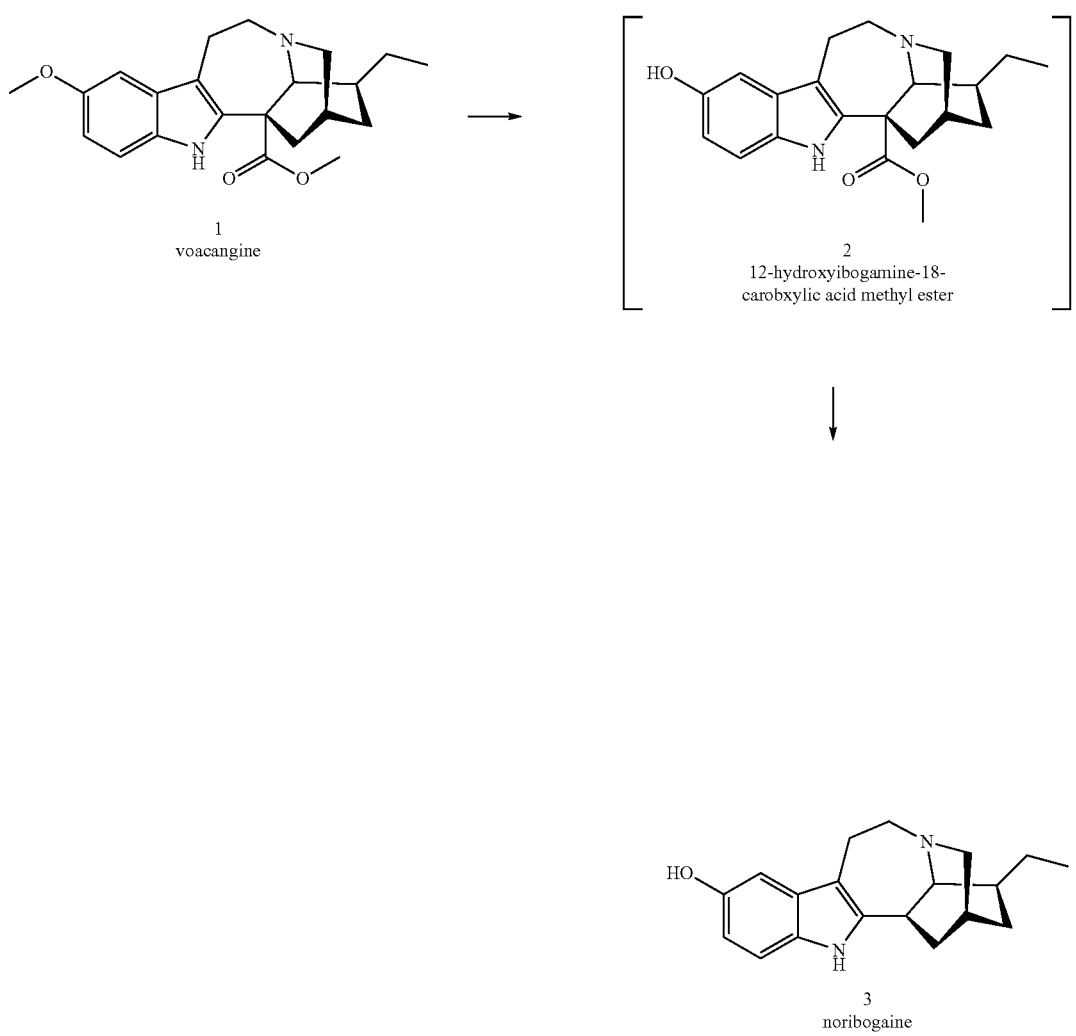

Voacangine 1 can be taken up in a dichloromethane/ethanethiol solution and cooled to 0 to −10° C. (ice salt bath). An excess (1-3 molar equivalents) of a suitable Lewis acid (boron trichloride, boron tribromide or aluminum trichloride) is added portionwise. The resultant mixture is stirred at 25 to 50° C. for 2 to 24 hours until determined to be sufficiently complete by TLC. The reaction mixture can then be diluted with fresh dichloromethane, washed with a saturated NaHCO$_3$ solution, dried and evaporated under reduced pressure which is contemplated to provide the corresponding 12-hydroxyibogamine-18-carboxylic acid methyl ester 2, which may then be purified by silica gel column chromatography using a gradient of hexane and ethylacetate or used in the next step without purification.

A solution of 12-hydroxyibogamine-18-carboxylic acid methyl ester 2 as provided above in a potassium/methanol solution can be heated and held at reflux for about 6 hours, at which time the solvent can be stripped, water added and the resulting aqueous solution is washed with ether, acidified to a pH of about 2 (conc HCl), and evaporated to dryness. The residue can then be taken up in a chloroform/methanol mixture and the potassium chloride filtered off to provide the hydrochloride salt of noribogaine 1. The free base of noribogaine can be obtained by basifying an aqueous solution of the hydrochloride salt of noribogaine 1 (e.g. with solid sodium bicarbonate, sodium carbonate, etc.) and extracting the basic aqueous solution with ether (at least 3×). the combined ethereal fractions can be combined and evaporated to provide noribogaine 1.

Example 2

Synthesis and Purification of Noribogaine from Voacangine Using Solid Support

Example 2 illustrates one method for the synthesis and purification of noribogaine from voacangine which method follows Scheme 6 below.

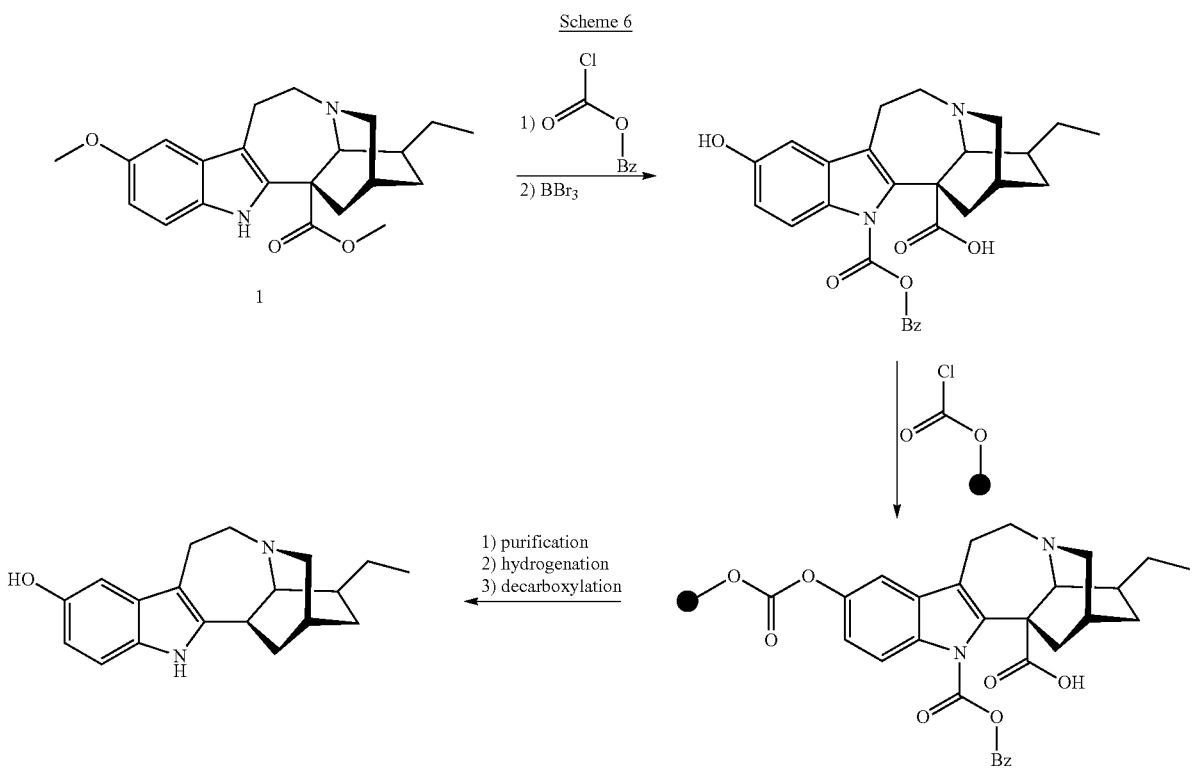

Scheme 6

Specifically, in Scheme 6, voacangine is contacted with a stoichiometric excess of benzyl chloroformate (BzCO$_2$Cl) in an inert solvent such as tetrahydrofuran. The reaction mixture further contains at least a stoichiometric equivalent of diisopropylethylamine relative to voacangine so as to scavenge the acid generated during the reaction. The reaction is maintained at room temperature under an inert atmosphere until the reaction is substantially complete as evidenced by, for example, thin layer chromatography. At which time, an O-demethylating reagent (e.g. boron tribromide or aluminum trichloride), and preferably a stoichiometric excess thereof, is added to the reaction mixture which is then maintained under suitable conditions (e.g. 0° C. to room temperature) wherein the aryl methoxy group of voacangine has been converted to the corresponding hydroxyl group. It is contemplated that under these reaction conditions, the methyl ester will de-esterify to provide the corresponding acid.

The phenol generated above is then employed as a complementary functionality for attachment of a solid support. In particular, an excess of chloroformate bound to a solid support is utilized under conventional conditions such that a cleavable carbonate bond is formed. Chloroformate bound to a solid support can be prepared from a hydroxy-bearing polymer support (e.g. hydroxymethyl)polystyrene or polymer-bound benzyl alcohol, both commercially available from Sigma-Aldrich®) and carbonyl dichloride.

In one particular example, 1 kg of solid support containing CBZ protected 12-hydroxyibogamine-18-carboxylic acid is loaded onto a column. The stopper of the column is partially opened so that a flow rate through the column of 0.5 liters per hour is maintained. Methylene chloride is continuously fed to the top of the column and recovered at the base of the column. The elution of fresh solvent is continued until the effluent no longer contains either of the unreacted starting materials. At which time, a portion of the solid support is loaded into a hydrogenation vessel together with methanol and a catalytic amount of palladium on carbon. Hydrogenation is continued under elevated pressure for approximately 5 hours. The reaction is then stopped and the methanol recovered and stripped to provide 12-hydroxyibogamine-18-carboxylic acid. Decarboxylation of 12-hydroxyibogamine-18-carboxylic acid can be accomplished using a metal (i.e. potassium, copper, etc.) in refluxing methanol. Additional purification/analysis of the resultant noribogaine 3 can be provided by HPLC as desired.

Example 3

Synthesis of Noribogaine from Voacangine via the Lithium or Sodium Salt

Example 3 illustrates one method for the synthesis of noribogaine from voacangine which method follows Scheme 6 below.

The conversion of voacangine 1 to Noribogaine 3 has been reported as early as 1957 (Janot and Goutarel, U.S. Pat. No. 2,813,873). This was done in either a one-step process in going from voacangine (1) to Noribogaine (3) using HOAc/HBr (48%, reflux) without separation of any intermediates, or via a two-step process starting with converting voacangine (1) to Ibogaine (KOMe), followed by converting the ibogaine to Noribogaine (3) (HBr, 48%/HOAc/reflux). This synthesis is reproducible, but we provide herein a process for 1 to 3 that does not involve the intermediacy of ibogaine.

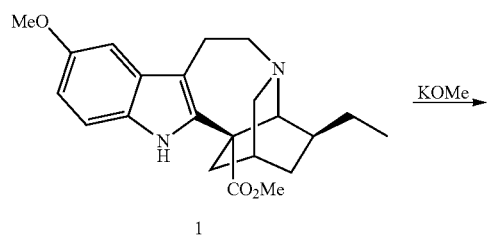

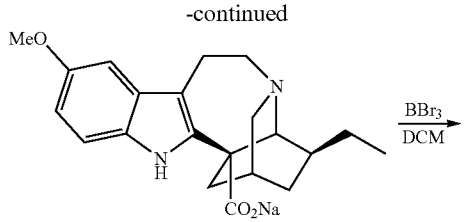

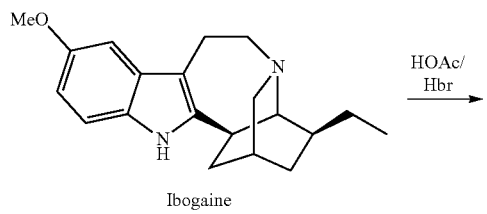

Ibogaine

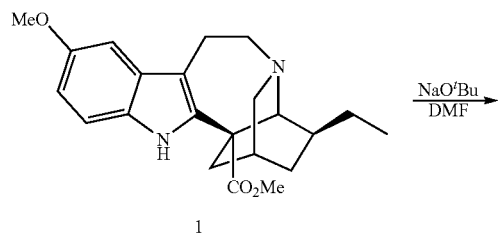

3

Sodium Voacanginecarboxylate Conversion to Noribogaine

Voacangine (1) can be converted to the voacanginic acid sodium salt (20) using a base, such as NaO$^t$Bu in DMF, followed by demethylation (e.g. BBr$_3$ or LiPPh$_2$) to yield Noribogaine (3).

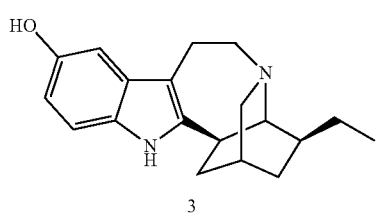

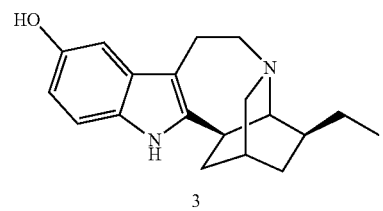

3

Lithium Voacanginecarboxylate Conversion to Noribogaine

The lithium salt of voacangine (21) can be prepared by treating voacangine (1) with n-butyllithium in hexane at 0° C. with 1-propanethiol (see, Kuehne, et al. *J. Med. Chem.*, 2003, 46, 2716-2730). The carboxylate anion and the lithium of 21 form a tight ion pair and thus compound 21 can be isolated and purified. The lithium salt of voacangine (21) can likewise be demethylated using, e.g., BCl$_3$ or BBr$_3$ in DCM, to provide compound 21a, and can then undergo decarboxylation under standard conditions, such as e.g., acid catalyzed decarboxylation using HBr or HCl, to provide noribogaine 3. Both compounds 21 and 21a can be isolated and purified as compounds per se. The noribogaine 3 can be isolated as the free base or a salt thereof, such as the hydrochloride or hydrobromide salt thereof. In one embodiment, the noribogaine is isolated as noribogaine hydrochloride. In another embodiment, the noribogaine is isolated as noribogaine hydrobromide. One of skill in the art could readily interchange the anion using conventional methods.

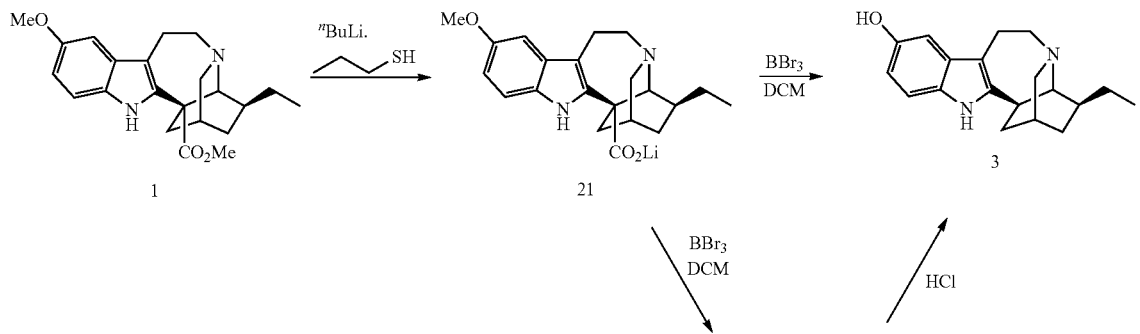

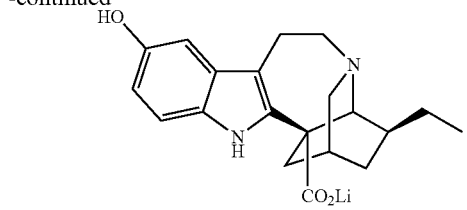

Other Approaches Under Investigation for Ibogaine-Free Production of Noribogaine The voacanginecarboxylate salts (20 or 21) can be converted into other carboxyl group protected derivatives that can be demethylated and deprotected to yield Noribogaine 3.

For example, protected derivatives include benzyl protected voacanginecarboxylate (22) (which can be deprotected using catalytic hydrogenation), and the allyl protected voacanginecarboxylate (23) (which can be deprotected with Pd(IV), A-ring demethylation) can be utilized as intermediates.

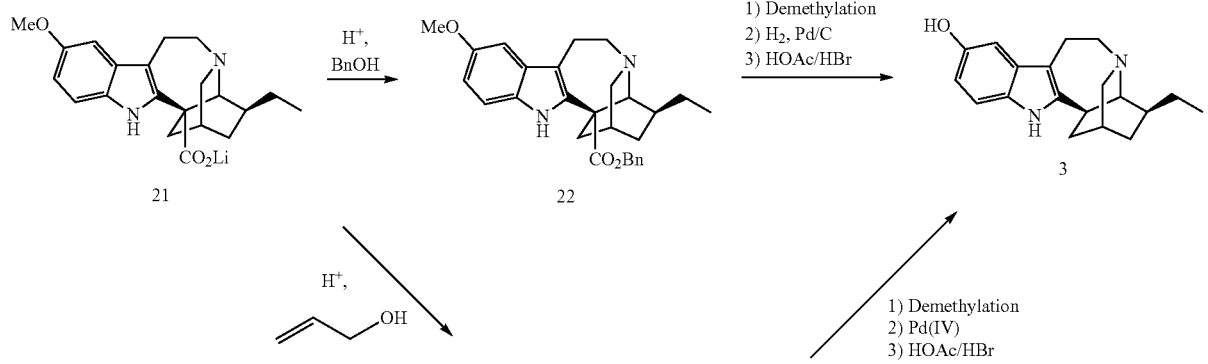

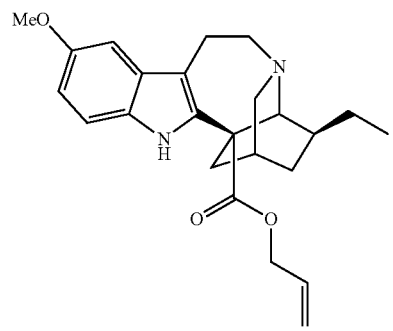

What is claimed is:

1. A solid support having voacangine, 12-hydroxyibogamine-18-carboxylic acid methyl ester, 12-hydroxyibogamine-18-carboxylic acid or the carboxylic acid salt thereof, covalently bound thereto through a cleavable linker.

2. A compound of the formula:

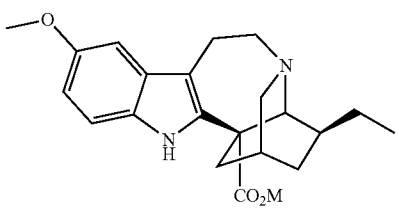

where M is lithium, sodium or potassium.

3. A compound of the formula:

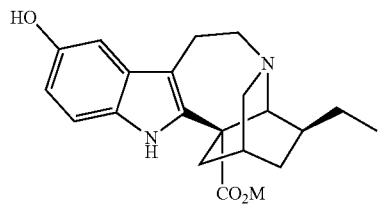

where M is lithium, sodium or potassium.

4. The compound of claim 2 or claim 3, wherein M is lithium.

* * * * *